United States Patent [19]
Conta et al.

[11] Patent Number: 5,405,389
[45] Date of Patent: Apr. 11, 1995

[54] SINTERED COATINGS FOR IMPLANTABLE PROSTHESES

[75] Inventors: Robert L. Conta, Wilton; Alfred F. DeCarlo, Jr., Stamford; Douglas G. Noiles, New Canaan, all of Conn.

[73] Assignee: Joint Medical Products Corporation, Stamford, Conn.

[21] Appl. No.: 19,417

[22] Filed: Feb. 18, 1993

Related U.S. Application Data

[63] Continuation-in-part of Ser. No. 7,802, Jan. 22, 1993, Pat. No. 5,263,986, which is a continuation of Ser. No. 838,577, Feb. 19, 1992, abandoned.

[51] Int. Cl.$^6$ .............................. A61F 2/28
[52] U.S. Cl. ........................ 623/16; 623/66
[58] Field of Search ............ 623/18, 16, 23, 11, 623/22

[56] References Cited

U.S. PATENT DOCUMENTS

| | | |
|---|---|---|
| 3,605,123 | 9/1971 | Hahn . |
| 3,852,045 | 12/1974 | Wheeler et al. ............ 623/66 |
| 4,017,911 | 4/1977 | Kafesjian et al. ............ 623/2 |
| 4,156,943 | 6/1979 | Collier . |
| 4,206,516 | 6/1980 | Pillier . |
| 4,542,539 | 9/1985 | Rowe, Jr. et al. . |
| 4,629,464 | 12/1986 | Takata et al. . |
| 4,644,942 | 2/1987 | Sump ............ 623/16 |
| 4,713,076 | 12/1987 | Draenert . |
| 4,790,852 | 12/1988 | Noiles . |
| 4,813,965 | 3/1989 | Roberts . |
| 4,944,759 | 7/1990 | Mallory et al. ............ 623/22 |
| 5,178,201 | 1/1993 | Ahlers ............ 164/34 |
| 5,201,766 | 4/1993 | Georgette . |
| 5,258,030 | 11/1993 | Wolfarth et al. ............ 623/16 |
| 5,263,986 | 11/1993 | Noiles et al. . |

FOREIGN PATENT DOCUMENTS 2911754 10/1980 Germany .

*Primary Examiner*—David Isabella
*Attorney, Agent, or Firm*—Maurice M. Klee

[57] ABSTRACT

A sintered coating (13) for an implantable prosthesis (10) is provided having 1) interstices into which tissue or bone can grow, and 2) increased surface roughness which provides enhanced initial press-fit fixation. In certain embodiments, the coating includes at least two sets of particles (46,48) having different mean diameters. The sizes and numbers of particles are chosen so as to produce a matrix of smaller particles (48) in which are embedded a lesser number of spaced-apart larger particles (46). The smaller particles (48) provide support for the larger particles (46), and the larger particles (46) stand proud of the smaller particles (48) to provide the enhanced surface roughness. In other embodiments, the coating includes both generally smaller spherically-shaped (SS) particles and generally larger non-spherically-shaped (NSS) particles, with the NSS particles providing enhanced surface roughness and the SS particles providing support for the NSS particles.

9 Claims, 3 Drawing Sheets

0.006

0.025

0.010

SINTERED COATINGS FOR IMPLANTABLE PROSTHESES

CROSS-REFERENCE TO RELATED APPLICATIONS

This application is a continuation-in-part of U.S. application Ser. No. 08/007,802, filed Jan. 22, 1993, now U.S. Pat. No. 5,263,986, which is a continuation of U.S. application Ser. No. 07/838,577, filed Feb. 19, 1992, now abandoned.

BACKGROUND OF THE INVENTION

1. Field of the Invention

This invention relates to implantable prostheses and in particular to an improved sintered coating for such prostheses.

2. Description of the Prior Art

For at least the past twenty years, implantable prostheses have been coated with metal particles so as to provide a surface into which bone or tissue can grow. Such coatings have been applied by plasma spray and/or sintering. See, for example, Hahn, U.S. Pat. No. 3,605,123 and Pillier, U.S. Pat. No. 4,206,516. As a general rule, plasma spray coatings have a smaller void space than sintered coatings and thus are somewhat less preferred.

At present, a number of sintered coatings are in commercial use. The particles employed in these coatings are normally selected by sieving. They thus have a single-mode distribution about a mean diameter value. Typically, the mean value has been in the range from about 0.006 inches (150 microns) to about 0.040 inches (1000 microns). The breadth of the distribution about the mean will depend upon the sieves used to select the particles.

Sintered coatings of this type have been used in both single layer and multi-layer constructions. Also, they have been applied to prostheses having both smooth and stepped outer surfaces. See, for example, Noiles, U.S. Pat. No. 4,790,852.

One of the problems with the existing sintered coatings has been that relatively low levels of surface friction exist at the interface between the coating and the bone. Most prostheses are implanted by press fitting into a prepared cavity in the patient's bone. A high level of friction at the coating-bone interface is thus desirable because it helps provide a more stable initial fixation of the prosthesis in the prepared cavity. An initial stable fixation of the prosthesis has been found to increase the likelihood of bone ingrowth.

SUMMARY OF THE INVENTION

In view of the foregoing state of the art, it is an object of this invention to provide improved sintered coatings for implantable prostheses. More particularly, it is an object of the invention to provide sintered coatings which provide a high degree of surface friction at the coating-bone interface. It is a further object of the invention to provide improved coatings which can be readily manufactured using conventional techniques.

To achieve the foregoing and other objects, the invention provides a sintered coating having an irregular surface produced by the use of particles having at least a bimodal size distribution, as opposed to the single-mode size distribution used in the prior art. As used herein, the term "at least a bimodal size distribution" means that a plot of number of particles versus particle diameter has at least two discernible peaks. Such plots can be readily constructed using sieving techniques to construct a histogram or by simply counting and measuring particles for a representative portion of a coated prosthesis. In this connection, the diameter of a particle is defined as the longest chord between any two points on the surface of the particle.

In certain embodiments of the invention, the particles making up the coating are all substantially spherically-shaped, that is, their cross-sections are substantially circular. For ease of reference, such substantially spherically-shaped particles will be referred to herein and in the claims as simply "spherically-shaped particles" or as "SS particles."

In other embodiments, some of the particles are spherically-shaped while others have an irregular shape like that of grains of table salt. These particles are substantially aspherical, sometimes acicular, e.g., the particles may have cross-sections which are rhombic in form. For ease of reference, the irregularly-shaped particles will be referred to herein and in the claims as "non-spherically-shaped particles" or as "NSS particles." The above definition of the diameter of a particle is applicable to coatings containing only SS particles. When the coating contains both SS and NSS particles, the diameter of a particle is then defined as the diameter of the smallest hole through which the particle may pass.

In accordance with the invention, it has surprisingly been found that the use of smaller SS particles mixed with generally larger NSS particles provides a stronger sintered bond strength between the particles and the substrate than is obtained by the use of smaller NSS particles mixed with larger NSS particles. That is, the use of SS particles is critical to the effectiveness of the invention.

When SS and NSS particles are used, at least one of the peaks of the at least bimodal size distribution corresponds to SS particles while at least another of the peaks of the at least bimodal size distribution corresponds to NSS particles. For a size distribution having just two discernible peaks, i.e., a bimodal distribution, the smaller mean diameter preferably corresponds to the SS particles and the larger mean diameter preferably corresponds to the NSS particles. For a size distribution having more than two discernible peaks, i.e., a multi-mode distribution, there is preferably at least one peak corresponding to SS particles whose mean diameter is smaller than the smallest mean diameter of any of the peaks corresponding to the NSS particles, that is, there are preferably SS particles which are smaller than the NSS particles so that the SS particles can provide support for the NSS particles on the surface of the prosthesis.

The at least bimodal size distribution is preferably achieved by mixing together at least two sets of sieve-selected particles having different mean diameters. In general, it is preferred to select amounts of particles from the at least two sets so that the final distribution of particles includes more small particles than large particles. For example, for a coating made from two sets of sieve-selected particles, the ratio of the number of small particles to the number of large particles in the final distribution is preferably in the range from about 4:1 to about 40:1. When a combination of SS and NSS particles is used, the final distribution of particles can include approximately equal numbers of small and large particles. For example, the range of SS to NSS particles (SS:NSS) is preferably from about 1:1 to about 20:1.

When SS and NSS particles are used, the advantages of the invention can be achieved even though the mean diameters of the SS and NSS particles are approximately equal. Accordingly, for these embodiments, the size distribution of the particles making up the coating need not be at least bimodal as in the case when only SS particles are used.

The particle mixture of the invention is applied to a prosthesis using the conventional techniques employed with single-mode particle distributions. Accordingly, the invention can be readily put into practice with essentially no changes to existing manufacturing techniques, which represents an important advantage of the invention.

In certain preferred embodiments, the particles are applied in substantially a single layer. In other preferred embodiments, the single layer is applied to a prosthesis having a stepped outer surface.

In practice, it has been found that prostheses coated with SS particles having size distributions of the type disclosed herein have significantly higher levels of surface friction in comparison to prostheses coated with similar particles having a single-mode distribution. The combination of SS and NSS particles has been found to produce even higher levels of surface friction.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

Figure 3A:
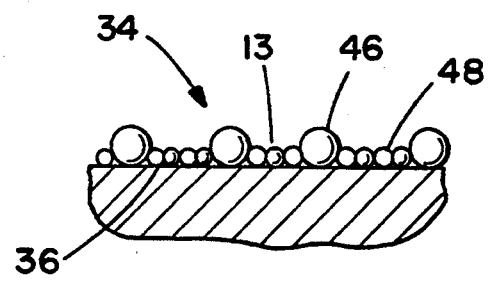
FIGS. 3A, 3B, and 3C are schematic diagrams illustrating representative constructions of coatings prepared in accordance with the invention.
Figure 3B:
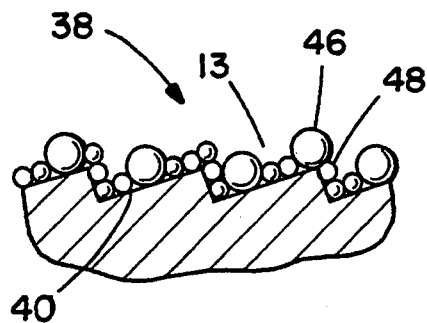
Figure 3C:
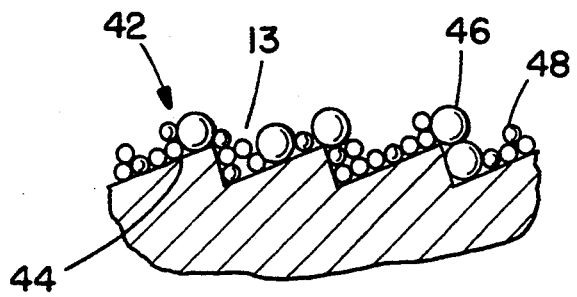
Figure 4:
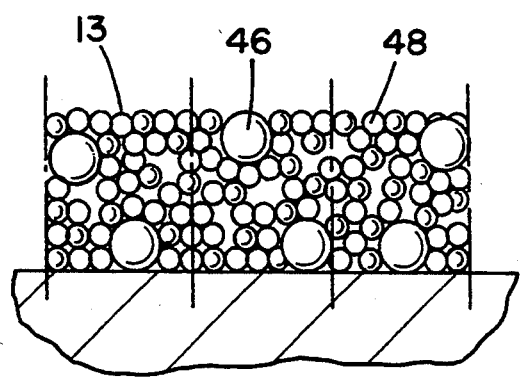
FIG. 4 is a plan view of the coatings of FIGS. 3B and 3C.

Although SS particles have been used for purposes of illustration in FIGS. 3 and 4, it is to be understood that the diagrams also apply to combinations of SS and NSS particles. In such embodiments, the larger particles shown in the figures are preferably NSS particles and the smaller particles are preferably SS particles.

Figure 5:
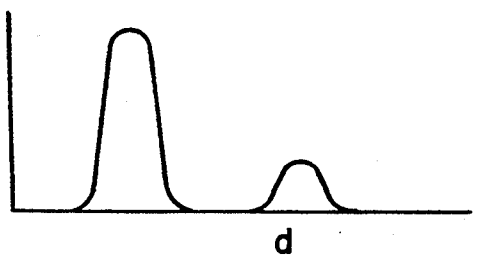

FIG. 5 shows the particle size distribution for the coatings of FIG. 3. As discussed above, for embodiments employing SS and NSS particles, both the mean diameter values (d) and the particle number values (n) for the two types of particles can be less disparate and in some embodiments either or both of these values can be substantially the same, i.e., $n_{SS}$ can be approximately equal to $n_{NSS}$ and/or $d_{SS}$ can be approximately equal to $d_{NSS}$.

Figure 6:
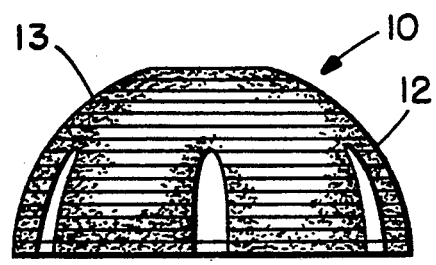

FIG. 6 shows an acetabular cup employing a coating of the invention.

Figure 7:
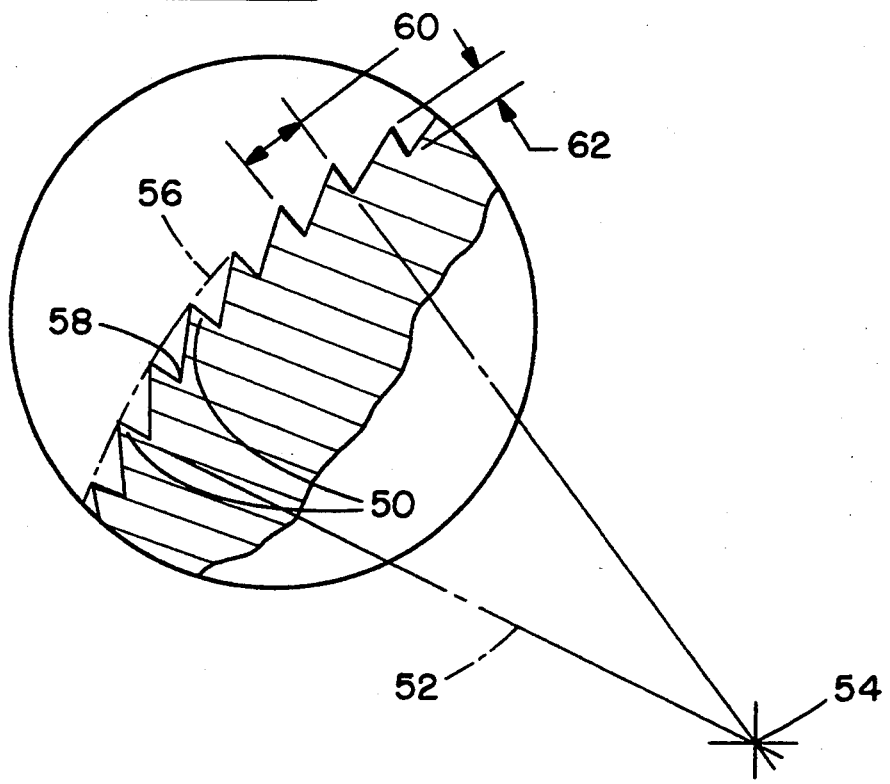

FIG. 7 is an expanded view of a portion of the surface of the acetabular cup of FIG. 6.

Figure 8:
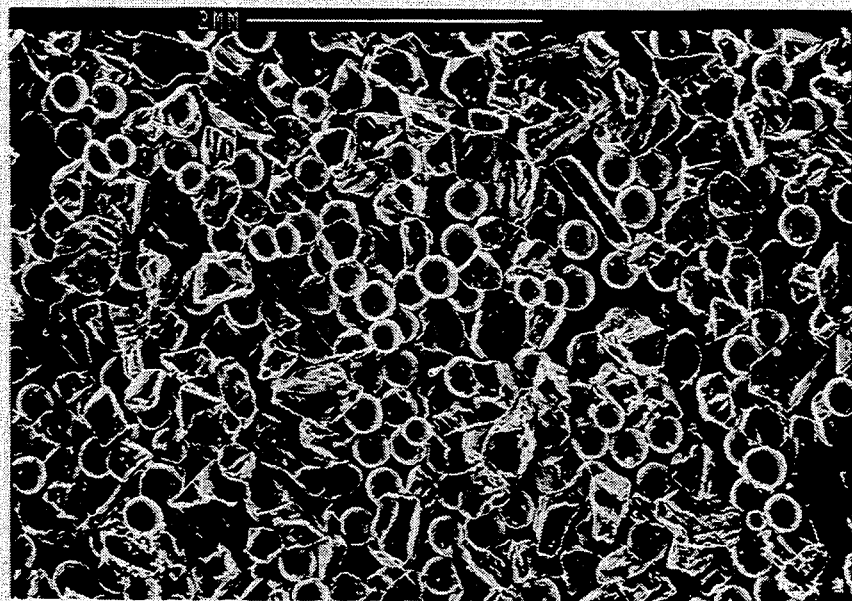
Figure 9:
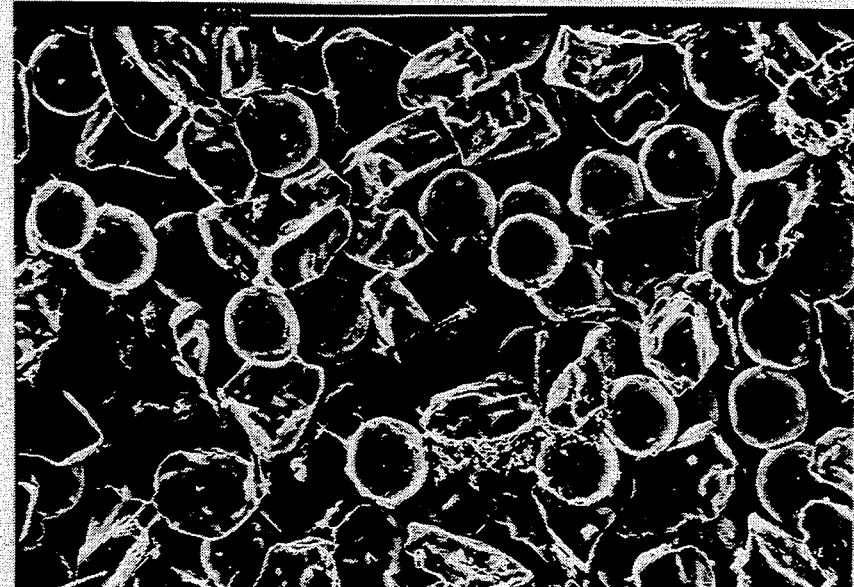

FIGS. 8 and 9 are photomicrographs showing a coating prepared in accordance with the invention and having SS and NSS particles. The magnification in FIG. 8 is 20× while that in FIG. 9 is 40×.

DESCRIPTION OF THE PREFERRED EMBODIMENTS

As described above, the present invention relates to an improved sintered coating for implantable prostheses. The invention can be applied to all types of metal prostheses now known or subsequently developed, including, for example, hip and knee joint replacement prostheses. As an example, FIG. 6 shows an acetabular cup 10 having a body 12 and a coating 13 constructed in accordance with the invention.

The sintered metal coating is composed of a biocompatible metal, such as, pure titanium, a titanium alloy (e.g., Ti 6Al 4V; ASTM-F136), or a cobalt-chromium alloy (ASTM-F75). Typically, the metal coating will have the same composition as that of the underlying prosthesis.

The coating is applied to the prosthesis using conventional sintering techniques known in the art. The sintering is performed in a high temperature, vacuum furnace. The particles are applied to the prosthesis in a binder which is volatilized during the sintering process. Various companies provide coating services for metal prostheses which can be used in the practice of the invention, including Bio-Vac Inc. (Southfield, Mich.), Hy-Vac Technologies, Inc. (Detroit, Mich.), and Astro Met, Inc. (Cincinnati, Ohio).

I. SS/SS Coatings

In accordance with certain embodiments of the invention, the surface of the coating is made irregular through the use of SS particles having at least a bimodal size distribution (referred to herein as an "at least bimodal SS/SS coating" or simply an "SS/SS coating"). Preferably, the bimodal size distribution is obtained by forming a mixture of at least two sets of sieve-selected particles having different mean diameters. The mixture is then used to coat the prosthesis.

The mean diameters for the at least two sets of particles and the numbers of particles from the sets are chosen so that 1) the final surface has spaced-apart larger particles embedded in a matrix of smaller particles, and 2) the larger particles stand proud of the smaller particles. The spaced-apart larger particles provide the desired roughness for the final surface. The smaller particles provide support for the larger particles so that the larger particles can resist the shear forces encountered during implantation and use of the prosthesis.

In contrast, if SS particles having a single-mode distribution were used to form a spaced-apart pattern having the same degree of roughness, the result would be a surface coating having many particles standing alone and therefore having only one point of integration with the prosthesis. Such isolated particles would have low shear strength and would be unsuitable for implantation in the body. The provision of a matrix of smaller particles solves this problem by providing numerous points of integration for each of the particles, i.e., both the smaller and the larger particles. The result is a strong, integrated coating having high shear strength. Moreover, the combination of at least two sets of particles produces a surface having numerous voids into which bone or tissue can grow.

Although the invention can be practiced with more than two sets of particles, for most applications a two set system will be adequate. To achieve 1) spaced-apart larger particles in a matrix of smaller particles and 2) larger particles standing proud of smaller particles, the larger particles for a two set system will generally have a mean diameter in the range of from about 2 to about 7 times the mean diameter of the smaller particles. Also, the number of smaller particles will be generally between about 4 and about 40 times the number of larger particles.

Furthermore, to insure that the larger particles stand proud of the smaller particles, the coating thickness should at most be a few layers and preferably should approach a single layer. Along these same lines, a stepped surface is preferred since the steps provide additional points of integration for the particles and contribute to the overall irregularity (roughness) of the final surface.

In practice, a mixture of equal measured volumes of 1) particles having a mean diameter of approximately 0.010 inches (250 microns), and 2) particles having a mean diameter of approximately 0.025 inches (630 microns), both determined by sieving, has been found to work successfully. For the particular particles used, the diameter range for the smaller particles was between about 0.007 inches (180 microns) and about 0.013 inches (330 microns), and the distribution for the larger particles was between about 0.017 inches (430 microns) and about 0.028 inches (710 microns).

In terms of particle numbers, if comparable packing configurations are assumed for the two sizes, the equal volumes correspond to a smaller particle to larger particle ratio of approximately 16:1. The use of particles of this type in a substantially single layer on a stepped surface has been found to result in a surface roughness substantially greater than that achieved with a single mode distribution of particles having a mean diameter anywhere in the range from about 0.010 inches (250 microns) to about 0.040 inches (1000 microns).

II. SS/NSS Coatings

In accordance with other embodiments of the invention, the surface of the coating is made irregular through the use of both SS and NSS particles (referred to herein as an "SS/NSS coating"). Coatings of this type can be applied to the surface of a prosthesis in single layer or multiple layer configurations.

As with the coatings employing only SS particles, the coatings employing SS and NSS particles can have an at least bimodal distribution and that distribution can be obtained by forming a mixture of at least two sets of sieve-selected particles having different mean diameters. Alternatively, the distribution can be substantially unimodal, although still formed by mixing two sets of sieve-selected particles, with one set being of SS particles and the other of NSS particles.

The SS particles of an SS/NSS coating provide support for the NSS particles. They thus perform a similar function to that performed by the smaller particles of an at least bimodal SS/SS coating. In conformance with that function, the SS particles of an SS/NSS coating preferably have a mean diameter which is at least somewhat smaller than the mean diameter of the NSS particles. The difference in mean diameters, however, need not be so large as to result in two distinct peaks on a particle size distribution plot, although, if desired, the difference may be so large.

Since the NSS particles inherently provide surface roughness because of their non-spherical shape, the NSS particles of an SS/NSS coating need not be spaced-apart like the larger SS particles of an at least bimodal SS/SS coating. Accordingly, the numbers of SS and NSS particles in an SS/NSS coating need not be as disparate as in an SS/SS coating and in the preferred embodiments of the invention, the numbers of SS and NSS particles are substantially equal in the final coating.

Because SS particles tend to adhere and integrate into the coating more readily than NSS particles during the coating process, such substantially equal numbers of SS and NSS particles can be achieved by beginning with an unequal mixture of particles. For example, to achieve a 50:50 mixture in the final coating, it has been found preferable to apply a 70:30 (NSS:SS) mixture to the surface of the prosthesis which is to be coated. More generally, for any desired NSS:SS ratio in the final coating, a somewhat large ratio is preferably used in the mixture which is applied to the prosthesis to take account of the difference in adherence/integration of NSS particles compared to SS particles.

The NSS particles can be manufactured by various techniques suitable for forming irregular particles. For example, for particles composed of titanium, 6 Al, 4V (ASTM F-136), the desired irregular shape can be obtained by ball milling the material after it has been hydrogen embrittled, i.e., subjected to a hydride-dehydride process. The particles are then vacuum annealed to reestablish the F136 chemistry. Processing of this type is available from various companies including Powder Alloy Corp (Cincinnati, Ohio).

FIGS. 8 and 9 are photomicrographs showing an SS/NSS coating having NSS particles prepared in accordance with the foregoing procedure. In particular, the NSS particles had a nominal size range of from 0.0098 inches (250 microns) to 0.0234 inches (600 microns) as defined by $-30$ $+60$ mesh sieve analysis. The SS particles used to prepare this coating had a nominal size range from 0.0083 inches (210 microns) to 0.0098 inches (250 microns) as defined by $-60$ $+70$ mesh sieve analysis. These SS particles were composed of titanium (ASTM F67).

The two particle types were mixed together in approximately a 70:30 ratio (NSS:SS) by volume and then applied to the sample surface, with a resulting approximately 50:50 particle type mixture on that surface. As shown in FIGS. 8 and 9, the coating mixture was applied in a single layer, although a multiple layer configuration can be used if desired. The coating was sintered to the substrate material using a heating cycle that gave a 25 MPa minimum shear strength and tensile strength when measured by the ASTM 1044 and 1147 methods.

The roughness of the surface produced through the use of SS and NSS particles is evident from the photomicrographs of FIGS. 8 and 9.

III. The Bimodal Size Distribution

The differences between the particle distribution for the at least bimodal coatings of the invention (whether of the SS/SS or of the SS/NSS type) and the particle distributions for prior art coatings is illustrated in FIGS. 1 through 5.

Figure 1A:
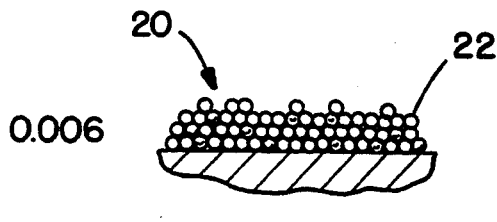
FIGS. 1A, 1B, and 1C are schematic diagrams illustrating typical constructions of prior art coatings.
Figure 1B:
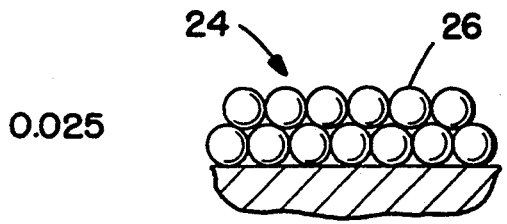
Figure 1C:
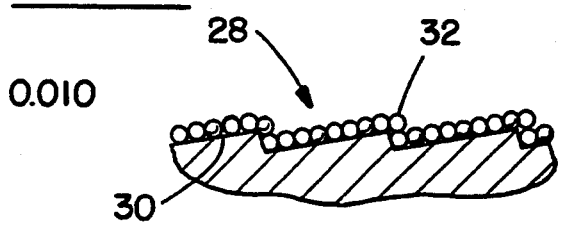

FIG. 1 shows cross-sectional views through typical coatings used in the prior art. More particularly, FIG. 1A shows a multi-layer construction 20 using relatively fine particles 22, e.g., particles having a mean diameter of about 0.006 inches (150 microns), FIG. 1B shows a multi-layer construction 24 using somewhat larger particles 26, e.g., particles having a mean diameter in the range from about 0.025 inches (630 microns) to about 0.040 inches (1000 microns), and FIG. 1C shows a single layer construction on a stepped prosthesis surface 30 using particles 32 having a mean diameter of about 0.010 inches (250 microns).

Figure 2A:
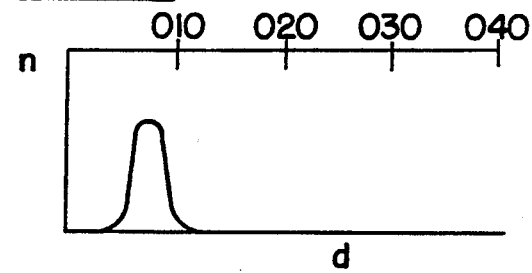
FIGS. 2A, 2B, and 2C show particle size distributions for the constructions of FIGS. 1A, 1B, and 1C, respectively.
Figure 2B:
Figure 2C:
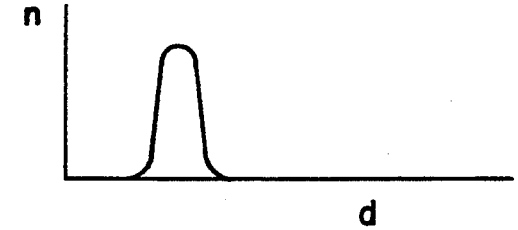

Representative plots of number of particles (n) versus particle diameter (d) for the constructions of FIGS. 1A, 1B, and 1C are shown in FIGS. 2A, 2B, and 2C, respectively. As shown therein, each of the distributions is single-moded, i.e., each distribution has one discernible peak.

FIG. 3 shows cross-sectional views through representative coatings constructed in accordance with the invention using two sets of sieve-selected particles having different mean diameters. In particular, FIG. 3A shows a single-layer construction 34 on a prosthesis having a smooth outer surface 36, FIG. 3B shows a single-layer construction 38 on a prosthesis having a stepped outer surface 40, and FIG. 3C shows a multi-layer construction 42 on a prosthesis having a stepped outer surface 44. FIG. 4 shows a plan view of the coating 13 for the constructions of FIGS. 3B and 3C. It should be noted in each of these figures that the distribution of the larger particles 46 within the matrix of the smaller particles 48 is substantially random.

FIG. 5 is a plot of number of particles (n) versus particle diameter (d) for the constructions of FIG. 3. As shown in this figure, the distribution is bimodal, i.e., there are two discernible peaks in this figure. It should be noted that although the valley between the peaks in this figure drops to zero, in general, the distributions for the two sets can overlap so that the valley need not go all the way to zero. Also, if more than two sets of particle sizes are used, the n versus d plot will have more than two peaks.

It should be noted that for SS/NSS coatings, the single layer, multi-layer, and stepped outer surface embodiments shown in FIGS. 3 and 4 can be used for particle distributions which are substantially unimodal, i.e., for particle distributions which are not at least bimodal.

IV. Stepped-Surface Prosthesis

As discussed above, the coatings of the invention whether of the SS/SS or the SS/NSS type can be used with prostheses having stepped surfaces. FIG. 7 shows a preferred construction for the stepped surface of FIG. 3C when used on a spherically-shaped cup of the type shown in FIG. 6.

As illustrated in this figure, the cross-sectional shape of each step 50 is oriented similarly relative to a radial line 52 emanating from the center 54 of the sphere 56. This construction allows all of the steps to have a similar shape irrespective of their azimuthal location on the surface of the sphere. It also reinforces the adherence of the coating to the prosthesis when implanted in bone since the forces between the bone and the coating tend to drive the particles into the corners 58 of the steps.

Preferably, the steps have azimuthal spacings 60 and radial depths 62 on the order of 2.5 millimeters or less and 1.0 millimeters or less, respectively.

A variety of modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. A prosthesis for implantation in a body having an outer surface at least a portion of which has a sintered coating comprising a random mixture of at least two sets of metallic particles one of said at least two sets being composed of spherically-shaped particles and another of said at least two sets being composed of non-spherically-shaped particles, wherein:

(a) the coating comprises less than two complete layers of particles;
   (b) there are sintered junctions between the spherically-shaped particles and the non-spherically-shape particles; and
   (c) the set composed of spherically-shaped particles has a smaller mean diameter than the mean diameter of the set composed of non-spherically-shaped particles.

2. The prosthesis of claim 1 wherein the portion of the outer surface which has the sintered coating is stepped.

3. The prosthesis of claim 1 wherein the coating comprises substantially a single layer of particles.

4. The prosthesis of claim 1 wherein the at least two sets of metallic particles have a size distribution which is at least bimodal such that the size distribution includes at least two discernible peaks.

5. The prosthesis of claim 4 wherein the diameters of the spherically-shaped particles are in the range from about 210 microns to about 250 microns and the diameters of the non-spherically-shaped particles are in the range from about 250 microns to about 600 microns.

6. The prosthesis of claim 1 wherein the ratio of the number of spherically-shaped particles to the number of non-spherically-shaped particles is between about 1:1 and about 20:1.

7. The prosthesis of claim 1 wherein the ratio of the number of spherically-shaped particles to the number of non-spherically-shaped particles is approximately 1:1.

8. The prosthesis of claim 1 wherein the coating is formed using a mixture of a volume of spherically-shaped particles and a volume of non-spherically-shaped particles, the volume of non-spherically-shaped particles being greater than the volume of spherically-shaped particles.

9. The prosthesis of claim 8 wherein the ratio of the volume of non-spherically-shaped particles to the volume of spherically-shaped particles is approximately 70:30.

* * * * *